US011135331B2

(12) United States Patent
Rohner et al.

(10) Patent No.: US 11,135,331 B2
(45) Date of Patent: Oct. 5, 2021

(54) PROCESS FOR THE PREPARATION OF A STERILIZED CERAMIC BODY COMPRISING OR ESSENTIALLY CONSISTING OF STABILIZED ZIRCONIA OF A DEFINED COLOUR

(71) Applicant: STRAUMANN HOLDING AG, Basel (CH)

(72) Inventors: Adrian Rohner, Basel (CH); Simon Berner, Basel (CH); Marc Stephan, Basel (CH)

(73) Assignee: STRAUMANN HOLDING AG, Basel (CH)

(*) Notice: Subject to any disclaimer, the term of this patent is extended or adjusted under 35 U.S.C. 154(b) by 387 days.

(21) Appl. No.: 16/065,885

(22) PCT Filed: Dec. 22, 2016

(86) PCT No.: PCT/EP2016/082447
§ 371 (c)(1),
(2) Date: Jun. 25, 2018

(87) PCT Pub. No.: WO2017/109112
PCT Pub. Date: Jun. 29, 2017

(65) Prior Publication Data
US 2019/0001011 A1 Jan. 3, 2019

(30) Foreign Application Priority Data
Dec. 24, 2015 (EP) ..................................... 15202692

(51) Int. Cl.
A61L 2/28 (2006.01)
A61C 13/08 (2006.01)
(Continued)

(52) U.S. Cl.
CPC .................. A61L 2/28 (2013.01); A61C 5/77 (2017.02); A61C 8/0012 (2013.01);
(Continued)

(58) Field of Classification Search
CPC ....... C04B 35/486; C04B 41/80; C04B 35/48; C04B 41/0045; C04B 41/009;
(Continued)

(56) References Cited

U.S. PATENT DOCUMENTS 6,165,925 A  12/2000 Rieger
8,870,572 B2 * 10/2014 Mayer .................... A61B 17/68
                                          433/173
(Continued)

FOREIGN PATENT DOCUMENTS

WO  2015/025656 A1  2/2015
WO  2015/162554 A1  10/2015

OTHER PUBLICATIONS

Apr. 25, 2017 International Search Report issued in International Patent Application No. PCT/EP2016/082447.
(Continued)

Primary Examiner — Regina M Yoo
(74) Attorney, Agent, or Firm — Oliff PLC

(57) ABSTRACT

A process for the preparation of a sterilized ceramic body including or essentially consisting of stabilized zirconia of a defined colour, including the steps of: providing a ceramic primary body including or essentially consisting of stabilized zirconia of a first colour A, and sterilizing the primary body using radiation sterilization whereby the primary body undergoes a colour change to a colour B. The process includes the further step of irradiating the sterilized primary body with electromagnetic radiation of at least one wavelength lying in the wavelength band ranging from 150 nm to 700 nm to induce an at least partial reversal of the colour (Continued)

change to obtain a colour C of the sterilized ceramic body, the colour C complying with the following requirements in the CIELAB colour space: L* being from 54 to 95, a* being from −15 to 15 and b* being from −15 to 15.

16 Claims, 5 Drawing Sheets

(51) Int. Cl.
    *A61C 13/083*     (2006.01)
    *B65B 55/16*     (2006.01)
    *A61C 5/77*     (2017.01)
    *A61C 8/00*     (2006.01)
    *C04B 41/00*     (2006.01)
    *C04B 35/486*     (2006.01)
    *C04B 41/80*     (2006.01)
    *A61L 2/08*     (2006.01)
    *A61K 6/15*     (2020.01)
    *A61K 6/818*     (2020.01)
    *A61K 6/822*     (2020.01)
    *A61L 2/10*     (2006.01)
    *B65B 5/04*     (2006.01)
    *C04B 35/48*     (2006.01)
    *C04B 111/00*     (2006.01)
    *C04B 111/82*     (2006.01)

(52) U.S. Cl.
    CPC .......... *A61C 8/0087* (2013.01); *A61C 13/082* (2013.01); *A61C 13/083* (2013.01); *A61K 6/15* (2020.01); *A61K 6/818* (2020.01); *A61K 6/822* (2020.01); *A61L 2/081* (2013.01); *A61L 2/084* (2013.01); *A61L 2/10* (2013.01); *B65B 5/04* (2013.01); *B65B 55/16* (2013.01); *C04B 35/48* (2013.01); *C04B 35/486* (2013.01); *C04B 41/009* (2013.01); *C04B 41/0045* (2013.01); *C04B 41/80* (2013.01); *A61C 2202/00* (2013.01); *A61L 2202/21* (2013.01); *C04B 2111/00836* (2013.01); *C04B 2111/82* (2013.01); *C04B 2235/3225* (2013.01); *C04B 2235/3246* (2013.01); *C04B 2235/3272* (2013.01); *C04B 2235/665* (2013.01); *C04B 2235/9661* (2013.01)

(58) Field of Classification Search
    CPC ... C04B 2235/3225; C04B 2111/00836; C04B 2235/3272; C04B 2235/665; C04B 2111/82; C04B 2235/3246; C04B 2235/9661; A61C 8/0087; A61C 8/0012; A61C 13/082; A61C 13/083; A61C 5/77; A61C 2202/00; B65B 5/04; B65B 55/16; A61L 2/28; A61L 2/081; A61L 2/084; A61L 2/10; A61L 2202/21; A61K 6/15; A61K 6/818; A61K 6/822
    See application file for complete search history.

(56) References Cited

U.S. PATENT DOCUMENTS

| | | | |
|---|---|---|---|
| 2009/0317768 A1* | 12/2009 | Mayer | A61B 17/68 433/201.1 |
| 2015/0012091 A1* | 1/2015 | Mayer | A61B 17/68 623/11.11 |
| 2017/0260107 A1* | 9/2017 | Yilbas | C04B 41/5062 |

OTHER PUBLICATIONS

Apr. 25, 2017 Written Opinion of the International Searching Authority issued in International Patent Application No. PCT/EP2016/082447.

* cited by examiner

PROCESS FOR THE PREPARATION OF A STERILIZED CERAMIC BODY COMPRISING OR ESSENTIALLY CONSISTING OF STABILIZED ZIRCONIA OF A DEFINED COLOUR

The present invention relates to a process for the preparation of a sterilized ceramic body comprising or essentially consisting of stabilized zirconia of a defined colour.

The invention further relates to a sterilized ceramic body obtainable by the process as well as to the use of the sterilized ceramic body as a dental article, in particular as a component of a dental implant system, e.g. a dental implant or a dental implant abutment, or as a suprastructure to be mounted on the dental implant system.

In the field of oral implantology, the translucency and colour of the restorative material used is of paramount importance for obtaining a restoration closely resembling a natural tooth. This applies both to the dental implant system to be anchored in the jaw bone, namely the dental implant itself and optionally a dental implant abutment and any further (tertiary) part of the system, as well as to the suprastructure to be mounted on the dental implant system, i.e. to a crown and/or a bridge.

From an aesthetical point of view, ceramics are particularly well suited as restorative materials, because of their ability to provide excellent cosmetic results owed to their colour and their adequate reflection and transmission of light. This applies in particular to zirconia ceramics, which in addition are biocompatible and exhibit good mechanical strength when subjected to masticatory efforts.

A specific zirconia ceramic material having a sufficiently high mechanical strength is disclosed in U.S. Pat. No. 6,165,925, which relates to an yttrium-stabilized zirconia in predominantly tetragonal form for the production of a sintered semi-finished article as a starting material for the manufacture of a prosthesis.

In general, dental articles must be sterilized before being brought into contact with a patient's body. To this end, the dental article is typically sterilized and stored in a sterile packaging, which remains closed until use of the article by the dentist.

In theory, different sterilization techniques can be applied. According to the most common approach, the dental article is subjected to heat sterilization using steam. This technique is typically performed in a steam sterilizer (also referred to as autoclave) using steam typically having a temperature above 120° C. under pressure.

Heat sterilization is, however, not suitable if the dental article to be sterilized is heat-sensitive or if further heat-sensitive components are present during sterilization. For example, heat sterilization is not suitable for a dental implant which is already packaged, since the packaging material is typically sensitive towards the sterilization temperature applied. In addition, the use of steam is unsuitable if during sterilization components are present that are soluble in water.

According to a further commonly used technique, the dental article is subjected to plasma sterilization, e.g. using hydrogen peroxide gas plasma, or to ethylene oxide gas sterilization. These techniques are limited to applications where only the surface directly accessible to the sterilizing agent is to be sterilized. They are, however, unsuitable for sterilizing an already per-assembled dental article comprising dental article components that are closely fitting to one another, e.g. a dental implant per-assembled with its transfer piece, since these comprise surface portions that are not directly accessible to the sterilizing agent. If ethylene oxide gas is used as sterilizing agent, the technique has the further drawback of requiring relatively strict safety measures due the high toxicity of the sterilizing agent.

In theory, radiation sterilization techniques, in particular gamma-sterilization or X-ray sterilization, would be of particular interest, since they allow for an efficient sterilization of an already pre-assembled dental article in its final packaging without damaging the packaging. This is due to the ionizing radiation unfolding its sterilizing effect also in microgaps, which—as mentioned above—is inaccessible to a sterilizing gas or plasma. In particular, radiation sterilization allows a thorough sterilization of a dental article, even if it comprises dental article components that are screwed together.

However, if a dental article made of stabilized zirconia is to be sterilized, which is the ceramic material of choice for dental applications, gamma-radiation has shown to induce a colour change of the material from white to brownish-purple. Thus, the desirable aesthetic properties achievable by using a ceramic material are lost by irradiating the material using gamma-radiation.

In practice, dental articles are thus typically sterilized using the plasma sterilization or ethylene oxide gas sterilization techniques mentioned above. This requires the components of a dental article assembly to be packaged separately, which makes the whole packaging and sterilizing workflow complicated and prone to further contamination.

In search of a process circumventing the shortcomings of the plasma sterilization or ethylene oxide gas sterilization techniques, WO 2015/162554 suggests a process, in which a zirconia implant is sterilized by exposing it to high-energy radiation, said implant being after exposure subjected to a heat treatment, preferably at 125° C. for 6 hours. According to WO 2015/162554, a reversal of the radiation-induced discolouration to a white or natural looking colour shall be achieved by the heat treatment.

Similarly, WO 2015/025656 discloses a prosthesis containing zirconia, said article being gamma-sterilized and then subjected to a heat-treatment at a maximum temperature from 100° C. to 300° C., in order to turn the brown colour of the gamma-sterilized prosthesis to a whiter colour.

It has, however, been found that the heat-treatment according to WO 2015/162554 and WO 2015/025656 is insufficient for the zirconia to obtain the desired appearance, in particular the brightness and the colour of a natural tooth. Also, the harsh heat treatment conditions taught in these documents have a negative, if not damaging impact on the packaging of the dental implant as well as on the implant itself, which in particular under humid conditions can undergo an accelerated hydrothermal aging.

In particular in view of the sterilization of an already packaged dental article, the applicability of the processes according to WO 2015/162554 and WO 2015/025656 is further limited to articles, which are stored under dry conditions. They are, however, unfeasible for dental articles stored in an aqueous solution.

In consideration of the above, the problem to be solved by the present invention is to provide a simple and safe process for sterilizing a ceramic body comprising stabilized zirconia, yet achieving a desired colour of the body, in particular a colour matching with the surrounding after implantation, more particularly a colour resembling the one of a natural tooth.

Specifically, the process shall be feasible irrespective of the presence of any heat-sensitive and/or water sensitive components present during sterilization and shall further allow efficient sterilization if a direct contact of the sterilizing agent and the surface to be sterilized cannot be established, as it is for example the case if the ceramic body to be sterilized is packaged, e.g. a packaged dental article. More specifically, the process shall allow for a thorough sterilization even if the ceramic body to be sterilized is a pre-assembled dental article and/or is a dental article stored in an aqueous solution.

The problem is solved by the process according to claim 1. Preferred embodiments of the process are defined in the dependent claims.

According to the invention, the process comprises the subsequent steps of
a) providing a ceramic primary body comprising or essentially consisting of stabilized zirconia of a first colour A, and
b) sterilizing the primary body using radiation sterilization whereby the primary body undergoes a colour change to a colour B.

As reported before, colour A of the stabilized zirconia is before sterilization of the primary body typically white or whitish, such as off-white or ivory-coloured.

By sterilizing the primary body, this white or whitish colour turns into colour B, which typically is brownish-purple.

The colour change from colour A to colour B (in the following also referred to as "discolouration") is assumed to be induced by electron transitions at local defects in the crystal lattice of the stabilized zirconia. Specifically, it is assumed that intrinsic defects of the type $Y_{Zr}'O^*$ are induced by the radiation sterilization, which can be correlated with an optical absorption band at 2.63 eV, thus creating a purplish-grey hue. It is further assumed that the discolouration can additionally be attributed to extrinsic defects at 3.16 eV, relating to trace amounts of impurities and responsible for a yellowish-brown discolouration. In combination, these defects lead to the brownish-purple colour B, which is in any respect disadvantageous in view of the body's use as a dental article.

According to the present invention, it has surprisingly been found that by irradiating the sterilized primary body with electromagnetic radiation of at least one wavelength lying in the wavelength band ranging from 150 nm to 700 nm, an at least partial reversal of the discolouration incurred in step b) can be achieved, such that the colour of the body can be approximated or matched to a natural tooth colour.

The process of the present invention thus comprises the further step
c) irradiating the sterilized primary body with electromagnetic radiation of at least one wavelength lying in a wavelength band ranging from 150 nm to 700 nm to induce an at least partial reversal of the colour change of step b) to obtain a colour C of the sterilized ceramic body, said colour C complying with the following requirements in the CIELAB colour space:
L* being from 54 to 95,
a* being from −15 to 15 and
b* being from −15 to 15.

Without wanting to be bound by the theory, it is assumed that by the irradiation according to step c), the electron transitions responsible for the discolouration are reversed by recombination, thereby at least partially restoring the colour of the primary body prior to sterilization.

By irradiating the sterilized primary body with electromagnetic radiation in a spectrum ranging from UV to visible light, the process of the present invention is in clear distinction from the teaching according to WO 2015/025656; a heat-treatment as taught in WO 2015/025656 has neither found to be mandatory nor sufficient for obtaining the desired degree of discolouration reversal.

In contrast to WO 2015/025656, which specifically teaches a heat treatment at a temperature ranging from 100° C. to 300° C., the process of the present invention allows for much milder conditions for the discolouration reversal. In particular, the conditions can be chosen such that any heat-sensitive component present, such as e.g. the packaging of the body, which typically is a plastic ampule or blister packaging, is not harmed by the treatment according to step c), as it would be the case when performing a heat treatment at a temperature of 100° C. or higher. This is of particular relevance, since also the radiation sterilization of step b) can be performed on the body being packaged.

More specifically, the process of the present invention can even be used for dental articles, which are stored in aqueous solution; unlike the heat treatment mentioned in the state of the art, no issues regarding a boiling of the aqueous solution occur given the mild conditions allowed by the present invention.

Ultimately, the whole process can, thus, be applied on a pre-assembled and finally packaged body stored in an aqueous solution, in particular in water or in an aqueous 0.9% NaCl solution.

Although the effect achievable by the present invention is of particular relevance if the ceramic primary body is in the form of a dental article containing two or more dental article components, which are pre-assembled with one another, it is understood that the present invention also encompasses embodiments in which the ceramic body is a single dental article component.

The process of the present invention therefore not only results in superior results regarding discolouration reversal, but further allows for a much higher flexibility than when using a heat treatment, and in particular can be performed on a pre-assembled and finally packaged body, as mentioned above.

Any packaging that is translucent for electromagnetic radiation at the respective wavelength, and in particular is transparent, can be used in the context of the present invention. Specifically, the packaging can be a COC (cyclic olefin copolymer) packaging, e.g. a COC vial, as known to the person skilled in the art, or a polyethylene packaging, e.g. a polyethylene blister.

According to a preferred embodiment, the sterilized primary body is in step c) irradiated with electromagnetic radiation of at least one wavelength lying in the UVB to the visible range, particularly in the UVA to the near-UV short wavelength visible range. With regard to the visible range, it is particularly preferred that the wavelength used for the irradiation of step c) is in the blue range, the green range and/or the red range, and most preferably in the blue range, i.e. in a range encompassing a wavelength of about 470 nm.

In more specific terms, the at least one wavelength of the electromagnetic radiation preferably lies in the wavelength band from 150 nm to 700 nm, more preferably from 200 nm to 650 nm, still more preferably from 250 nm to 600 nm, even more preferably from 300 nm to 550 nm, even more preferably from 320 nm to 500 nm and most preferably from 350 nm to 495 nm.

With regard to the specific embodiment of the present invention, that the ceramic body to be sterilized and irradiated is in its finally packaged form, the optimal wavelength band can be influenced to a certain degree by the specific material of the packaging. For a ceramic body packaged in a COC packaging, for example, the wavelength band according to step c) has preferably a lower limit of about 310 nm, more preferably a lower limit of about 315 nm, and most preferably a lower limit of about 320 nm, since COC can absorb a substantial portion of radiation in a range from 200 nm to 320 nm. By irradiating with at least one wavelength higher than 315 nm, preferably higher than 320 nm, a more efficient discolouration can be achieved for this specific embodiment, since in this band, the absorption by the packaging material is much lower, if not inexistent. Further, any potential issue resulting from the heating of the packaging (owing to the absorption of energy) can be circumvented.

It has further been found that, in particular for a relatively thin body of small dimensions, discolouration reversal is achieved for the whole body, even if the direction of the incident radiation is kept constant during the whole irradiation period of step c). Thus, a primary body, of which only a front side is exposed to the electromagnetic radiation according to step c), also undergoes the same discolouration reversal on the far side of said front side. Ultimately, all sides of the body exhibit the same colour C irrespective of the angle of incidence of the electromagnetic radiation, which further contributes to the simplicity and the efficiency of the process. Nevertheless, for thicker bodies having a thickness of more than 1 mm, it can be preferred that the angle of incidence is changed during step c), in order to allow for a more homogenous distribution of irradiance of the body's surface. This can e.g. be obtained by rotating the sterilized primary body during irradiation.

Within the terminology used herein, the term "primary body" relates to the body before completion of the process, i.e. before sterilization according to step b) and before discolouration reversal according to step c).

The term "colour" as used in the context of the present invention is to be understood broadly and also includes the brightness of the body.

The CIELAB colour space (or CIE L*a*b* colour space), to which the present invention relates in defining the colour of the primary body, is well-known to a skilled person and relates to a colour space specified by the International Commission on Illumination ("Commission internationale de l'éclairage") for describing all the colours visible to the human eye.

The three coordinates of the CIELAB colour space represent the lightness of the colour (L*=0 yields black and L*=100 indicates diffuse white), its position between red and green (a*, negative values indicate green while positive values indicate red) and its position between yellow and blue (b*, negative values indicate blue and positive values indicate yellow).

Specifically, L*, a* and b* can be determined using a spectrophotometer, and more specifically by UltraScan PRO from HunterLab (Murnau am Staffelsee, Germany). More specifically, L*, a* and b* are determined in reflection mode with setting RSEX, i.e. Reflectance Specular Excluded, meaning that light directly reflected on the surface is filtered out.

As mentioned, colour C obtained in step c) complies with the following requirements:
L* being from 54 to 95,
a* being from −15 to 15 and
b* being from −15 to 15.

According to a preferred embodiment, L* is from 63 to 90, more preferably from 68 to 85, most preferably from 70 to 75.

It is further preferred that a* is from −10 to 10, more preferably from −6 to 6, and/or b* is from −5 to 15, more preferably from −1 to 11.

The process of the present invention encompasses both embodiments, in which the discolouration reversal achieved in step c) is only partial or at least approximately complete.

In the specific case, where discolouration reversal is at least approximately complete, colour C thus corresponds essentially to initial colour A of the primary body before sterilization. In terms of the CIELAB colour space, each of L*, a* and b* are according to this embodiment at least essentially identical for colour A and colour C and deviate from each other by an absolute value of less than 20, preferably less than 10, more preferably less than 5.

Apart from this embodiment, the present invention also encompasses processes in which discolouration reversal is carried out in manner such to keep a residual discolouring shading of the primary body. For example, the duration of the irradiation according to step c) is controlled such that discolouration reversal is stopped before completion, with the purpose of rendering an off-white or ivory shading to the body. According to this embodiment, colour A and colour C differ from each other, meaning that in the CIELAB colour space, at least one of L*, a* and b* of colour A differ from the respective value of colour C.

Apart from the duration of irradiation, also the irradiance of the electromagnetic radiation can be adjusted in a manner to achieve the radiant exposure required for obtaining the desired shading in step c). Also, the wavelength can be adapted for obtaining the desired shading. In this regard, it has been found that e.g. irradiation with electromagnetic radiation at 254 nm leads to a residual discolour shading of the primary body.

As mentioned, the process of the present invention can be applied on the body also when being in a packaged state. According to a specific embodiment of the present invention, the body to be sterilized is, thus, packaged, the packaging being at least partially permeable (or "translucent") to the electromagnetic radiation used in step c).

In particular with regard to the sterilization of a packaged body, more particularly a packaged body stored in an aqueous solution, it is particularly preferred that step c) is carried out at a temperature below 100° C., more particularly below 60° C., and most particularly around or at room temperature. Thus, the at least partial reversal of the colour change in step b) is according to this embodiment solely achieved by the irradiation according step c), but not by any heat treatment. In this regard, it can further be preferred that after step c) any heat treatment step, in particular at 100° C. or more, more specifically at 300° C. or more and most specifically at 500° C. or more, is omitted.

The present process can thus be applied, even if heat-sensitive components are present.

Specifically, the process can be applied on a packaged body that is held in solution (e.g. aqueous solutions) in the packaging, as it is for example the case for a dental implant which directly after surface roughening by means of sandblasting and acid etching is immersed in a solution to preserve the hydrophilic properties obtained by the surface roughening.

Regarding the material, the process according to the present invention relates to stabilized zirconia, and more specifically relates to stabilized zirconia comprising vacancies in the oxygen-sublattice of its crystal structure. As discussed above, the present invention allows discolouration phenomena to be efficiently reversed for this material, assumingly due to recombination of the electron transitions accountable for the discolouration.

By the primary body according to the present invention "comprising or essentially consisting of stabilized zirconia" both embodiments are encompassed in which the primary body consists of stabilized zirconia as the sole material as well as embodiments which apart from stabilized zirconia comprises a further material, e.g. a further ceramic component and/or a metal component. In analogy, the same applies to the sterilized ceramic body to be prepared by the process of the present invention.

By the term "stabilized zirconia" both fully stabilized zirconia as well as partially stabilized zirconia are encompassed. Depending on the determined use of the ceramic body, either fully stabilized zirconia or partially stabilized zirconia can be preferred.

According to a particularly preferred embodiment, the stabilized zirconia is yttria-stabilized zirconia, due to the mechanical and aesthetical properties, which make this material particularly suitable for its use in oral implantology.

In this regard, it is further preferred that the composition of the partially stabilized zirconia complies with the requirement that the total amount of $ZrO_2$, $Y_2O_3$ and $HfO_2$ is more than 99.0 weight-%, with the amount of $Y_2O_3$ being from 4.5 to 5.4 weight-%, with the amount of $Al_2O_3$ being less than 0.5 weight-% and the amount of $HfO_2$ being less than 5.0 weight-%.

More specifically, the yttria-stabilized zirconia used according to the present invention is in the tetragonal crystalline phase, owed to its ability for martensitic transformation and thus the intrinsic ability to respond to induced stress, namely to close cracks and/or to countervail crack propagation in the body.

Typically, the stabilized zirconia further contains impurities in the form of trace elements, which can give rise to extrinsic defects in the lattice of its crystal structure, and more particularly can contain Fe species, specifically Fe ions. It has been found that by the presence of trace elements, and of Fe ions in specific, the stabilized zirconia of the ceramic primary body exhibits an off-white or ivory colour shading, which can be desirable in view of achieving a natural tooth colour of the body. This initial shading can—after the colour change occurring in step b) —be obtained again by the discolouration reversal in step c). It has, however, been found that for a zirconia material comprising trace elements imparting such a shading, a longer irradiation duration is generally required in order to obtain the desired discolouration reversal.

According to a preferred embodiment, the zirconia used in the process of the present invention is at least approximately devoid of praseodymium.

According to a further preferred embodiment, the yttria-stabilized zirconia comprises apart from zirconia an amount of about 4.5 to 6 wt.-% of $Y_2O_3$, less than 5 wt.-% of $HfO_2$, about 0.1 to 0.4 wt.-% $Al_2O_3$, less than 0.02 wt.-% $SiO_2$, less than 0.01 wt.-% $Fe_2O_3$ and less than 0.04 wt.-% $Na_2O$. Specific examples of preferred types of zirconia include MZ111 (available from CeramTec GmbH) and Tosoh Zirconia (available from Tosoh Corporation).

Preferably, the precursor body is in step b) sterilized using ionizing radiation sterilization, preferably gamma-sterilization. As mentioned previously, gamma-sterilization is particularly preferred, since sterilization can be carried out in a very efficient manner. In particular, an efficient sterilization can be achieved, even if the body to be sterilized is already pre-assembled and packaged. Any risk for contamination, which might otherwise occur during subsequent assembly and packaging steps, can therefore be circumvented. Also, given the fact that gamma-sterilization can be performed at mild temperature conditions, the process can be carried out even if a heat-sensitive component, e.g. a heat-sensitive packaging, is present. The same applies to X-ray sterilization, which depending on the specific circumstances can also be preferred.

Additionally or alternatively to gamma-sterilization and/or X-ray sterilization, which are particularly preferred, other radiation sterilization techniques, such as beta-sterilization or e-beam sterilization, can be applied. In this regard, it has been found that the discolouration effect is particularly pronounced when using gamma-sterilization or X-ray sterilization, whereas a less intense, but nevertheless clearly observable discolouration effect is also detected for a primary body that is e-beam sterilized or beta-sterilized.

According to a specific embodiment of the process of the present invention, an activation of colour centers in the stabilized zirconia occurs in step b), thus inducing an excited state of said colour centers, and in step c) a transition of electrons of said colour centers from the excited state into a relaxed state is induced. Said relaxed state encompasses any state of lower energy compared to the excited state and in particular relates to the state before activation. Any stabilized zirconia in which colour centers are activated by radiation sterilization in general, and gamma-sterilization or X-ray sterilization in specific, can be used in the process of the present invention.

According to a further preferred embodiment, the sterilized precursor body is in step c) subjected to electromagnetic radiation at two or more different wavelengths both lying in the wavelength band ranging from 150 nm to 700 nm. For example, the precursor body can at the same time be subjected to electromagnetic radiation in the visible spectrum as well as to electromagnetic radiation in the UV spectrum.

The present invention also encompasses embodiments in which in step c) the sterilized precursor body is additionally subjected to a heat treatment. In this regard, the heat treatment is typically carried out simultaneously to irradiating the primary body with electromagnetic radiation. It is, however, also possible to carry out the heat treatment before or after irradiating the primary body.

Combining irradiation with electromagnetic radiation within the meaning of step c) with an additional heat treatment can in particular be of interest when a faster processing time is to be achieved, in particular when the discolouration reversal aimed at in step c) is to be achieved within a shortened time frame.

Taking into consideration the above mentioned preferred features and the advantages which can thereby be achieved, a specific embodiment of the present invention relates to a process comprising the subsequent steps of a') providing a ceramic primary body comprising or essentially consisting of yttria-stabilized zirconia of colour A', said ceramic primary body being in the form of a dental article containing two or more dental article components that are pre-assembled with one another and being contained in an at least partially translucent packaging, b') sterilizing the primary body using gamma-sterilization whereby the primary body undergoes a colour change to a colour B', and c') irradiating the sterilized primary body with electromagnetic radiation of at least one wavelength lying in the wavelength band ranging from 320 nm to 500 nm to induce an at least partial reversal of the colour change of step b') to a colour C', colour C' complying with the following requirements in the CIELAB colour space:
L* being from 68 to 85,
a* being from −10 to 10 and
b* being from −5 to 15.

Specifically, colour C' is a colour closely resembling the one of a natural tooth. Preferably, L* is from 70 to 75.

With regard to this specific embodiment of the process of the present invention, the ceramic primary body according to step a') can in particular be a packaged dental article, more particularly a packaged pre-assembled dental implant that is stored in aqueous solution.

The preferred duration of irradiating the primary body depends on the material of the primary body, on the type of radiation sterilization used in step b) as well as on the specific electromagnetic radiation including its intensity.

According to a specific embodiment, irradiation according to step c) is preferably carried out using an ultrahigh pressure 130 W mercury lamp. For example, irradiation can be carried out using a lamp of the type "Nikon Intensilight C-HGFI Precentered Fiber Illuminator" using the mentioned ultrahigh pressure 130 W mercury lamp and featuring an optical fibre having a length of 1.5 m. With regard to the spectrum of this lamp, it is referred to the figures discussed below.

Apart from the mentioned Nikon Intensilight C-HGFI Precentered Fiber Illuminator, other lamps suitable for light irradiation include a Thorlabs Inc. OSL1-EC Fibre Illuminator using a halogen lamp with a colour temperature of 3200 K at maximum intensity and featuring an optical fibre providing a transmission from 340 nm to 800 nm.

For UV light irradiation, a conventional UV hand lamp (as e.g. available from Herolab GmbH Laborgeräte) or a UV light curing unit (as e.g. available from Heraeus-Kulzer Germany) can be used. Other UV-light sources include e.g. the UV lamp available under the tradename TFP-M/WL (of Vilber Lourmat).

According to another particularly preferred embodiment, irradiation is carried out by a device of the type Polylux-P (of Dreve Dentamid GmbH) featuring three 9 W lamps, specifically two of the type Osram Dulux X 9 W/78 and one of the type Osram Dulux S 9 W/71. The Polylux-P is relatively easy to handle and provides a simple and straightforward means for carrying out the irradiation of the present invention. Given the spectrum of the lamps, which for the 9 W/78 lies within 315 to 400 nm and for the 9 W/71 lies within 400 to 550 nm, the Polylux-P is also particularly suitable for the ceramic body being packaged in a COC or a polyethylene packaging, as mentioned above.

A device based on such commonly commercially available lamps, and on the Polylux-P in specific, allows to treat several ceramic bodies simultaneously. Thus, an up-scaling of the device for the simultaneous treatment of e.g. 100 or more ceramic bodies is easily possible and allows the treatment of whole production batches. On the other hand, a simple device, as e.g. the Polylux-P, can also very suitable be used in a dentist's surgery immediately prior to the dentist using the ceramic body as a dental article on the patient.

As will be discussed by way of the specific working examples, the discolouration reversal depends primarily on the wavelength of the electromagnetic radiation, with which the sterilized primary body is irradiated. Notwithstanding the primary relevance of the wavelength, the light intensity used has to some degree an impact on the optimum duration of irradiation.

In view of a relatively short duration of irradiation, the radiant flux received by the surface of the sterilized primary body is preferably of a relatively high flux density (or "irradiance"). According to a particularly preferred embodiment, the flux density of step c), i.e. the radiant flux received by the body's surface per unit area, is preferably at least 200 W/m$^2$, more preferably at least 500 W/m$^2$, and most preferably at least 1000 W/m$^2$.

When using the Intensilight lamp mentioned above, respective flux densities can be achieved by placing the body at a distance of 6.5 cm at most from the source (resulting in a flux density of more than 1'000 W/m$^2$) or, preferably, at a distance of 2.5 cm at most (resulting in a flux density of more than 20'000 W/m$^2$).

However, a sufficient colour change from colour B to C is also achievable using a lower radiant flux, achievable by less sophisticated devices than e.g. the Intensilight lamp.

It is understood that the optimum duration of irradiation depends on the specific wavelength of the electromagnetic radiation used in step c). Using the above-mentioned Intensilight lamp, the desired discolouration reversal can thus be achieved within a shorter time frame than when exposing the body to sunlight (with the solar constant $E_0$ being 1'367 W/m$^2$).

Also, the optimum duration can vary substantially between different materials of the ceramic body. For the above-mentioned embodiment, by which a flux density of about 20'000 W/m$^2$ is applied using the Intensilight lamp, an irradiation duration of as short as 10 minutes can be chosen for a ceramic body made of MZ111 to still achieve a sufficient discolouration reversal, whereas an even shorter irradiation duration (specifically in the range of a few minutes) can be chosen for a ceramic body made of Tosoh Zirconia to obtain the same effect. This allows the desired discolouration reversal to be performed in a very fast manner.

In many cases, however, a lower radiant flux (and therefore a less sophisticated irradiation device) will be sufficient to obtain the desired discolouration reversal, at the cost of a longer but nevertheless acceptable irradiation duration. This allows the process of the present invention to be easily up-scaled, in order to treat whole production batches simultaneously, as well as to be performed e.g. in a dentist's surgery immediately prior to unpacking the ceramic body and using it as a dental article on a patient.

The radiant exposure $H_e$ of the body's surface is defined by the following formula:

$$H_e = E_e t,$$

with $E_e$ being the irradiance of the surface (measured in W/m$^2$),
and t being the exposure duration (in s).

The radiant exposure needed to achieve a sufficient colour change depends on trace elements, e.g. Fe present in the ceramic material. For example, radiant exposures can differ by a factor of about 5 depending of the actual composition of the yttria-stabilized zirconia. In case of the MZ111 material, rather high radiant exposures are needed and are preferably in the range from 12 to 72 MJ/m$^2$, preferably from 18 to 62 MJ/m$^2$, more preferably from 24 to 55 MJ/m$^2$. Further experiments carried out on a ceramic body made of Tosoh Zirconia revealed that for this particular material also relatively low radiant exposures lead to a sufficient discolouration reversal.

According to a specific embodiment, the flux density is measured using a UV enhanced silicon photodiode, more specifically of the type SD100-13-23-222 (from advanced Photonix Inc.). In this regard, the current induced by the photodiode can be determined by implementing a current-voltage converter using an operation amplifier with a feedback resistor, as known to the skilled person.

Apart from the above described process, the present invention further relates to a sterilized ceramic body obtainable by the process.

According to a still further aspect, the present invention further relates to the use of the sterilized ceramic body as a dental article, since the advantages of the present invention, namely the combination of an efficient sterilization of stabilized zirconia with the obtaining of a desired colour, is of particular value in this technological field. In particular, the sterilized ceramic body can be used as a component of a dental implant system, more particularly a dental implant or a dental implant abutment, or as a suprastructure to be mounted on the dental implant system, more particularly a crown and/or a bridge.

In particular, the dental implant, the dental implant abutment or the suprastructure can be fully made of zirconia. Alternatively to these "fully-ceramic dental articles", the dental article can also be partially made of zirconia, as it is for example the case for a metallic dental implant comprising a ceramic ring made of zirconia.

The present invention is further illustrated by way of the following Examples.

EXAMPLES

Experimental Set I

For all examples, a ceramic primary body made of yttria-stabilized zirconia (3Y-TZP) having a ZLA® surface topography (comparable to the well-documented SLA® surface topography for titanium implants) was provided.

Of these, a first set of samples was gamma-sterilized using a Cobalt 60 source and a dose in the range of 25-42 kGy, and then directly subjected to different treatments, namely to UV treatment at 312 nm with 6*8 W
  for a duration of 1 minute,
  followed by a further duration of 10 minutes,
  followed by a further duration of 1 hour,
  followed by a further duration of 13 hours and 20 minutes,
  followed by a further duration of 5 hours and 25 minutes;
light treatment by exposure to a mercury light source (using a lamp of the type "Nikon Intensilight C-HGFI Precentered Fiber Illuminator", in the following referred to as "Intensilight lamp") for 257 minutes.

In addition, a second set of samples was packaged in a COC implant tube, gamma-sterilized using a Cobalt 60 source and a dose in the range of 25-42 kGy, and then exposed to the above mentioned light source according to the following protocol:

light treatment for 257 minutes;
light treatment by only using the fiber optics of the above-mentioned lamp (i.e. transporting the light through optical fiber such that the sample is irradiated with a point light source at full power) for 40 minutes of
  a sample packed in a COC implant tube without aqueous solution;
  a sample packed in a COC implant tube filled with $H_2O$; and
  a sample packed in a COC implant tube filled with 0.9% sodium chloride solution.

For comparative reasons, unpackaged samples of the first set have alternatively been subjected to the following treatment:

heat treatment at 121° C. for 30 minutes;
microwave treatment 800 W for a duration of 1 minute, followed by a duration of 4 minutes.

The sample as well as their respective treatment is summarized in the following Table 1.

TABLE 1

| Sample | Sterilization | Treatment after sterilization |
|---|---|---|
| 1a | Gamma-sterilization | UV treatment at 312 nm 6*8 W (1 minute) |
| 1b | Gamma-sterilization | UV treatment at 312 nm 6*8 W (+10 minutes) |
| 1c | Gamma-sterilization | UV treatment at 312 nm 6*8 W (+1 hour) |
| 1d | Gamma-sterilization | UV treatment at 312 nm 6*8 W (+13 hours and 20 minutes) |
| 1e | Gamma-sterilization | UV treatment at 312 nm 6*8 W (+5 hours and 25 minutes) |
| 2 | Gamma-sterilization | Light treatment (lamp) for 257 min. |
| 3 | Gamma-sterilization | Light treatment (lamp) of packaged sample for 257 min. |
| 4 | Gamma-sterilization | Light treatment (fiber optics) of packaged sample (stored dry) for 40 min. |
| 5 | Gamma-sterilization | Light treatment (fiber optics) of packaged sample (stored in H2O) for 40 min. |
| 6 | Gamma-sterilization | Light treatment (fiber optics) of packaged sample (stored in NaCl solution) for 40 min. |
| 7 (comparative) | Gamma-sterilization | heat treatment |
| 8 (comparative) | Gamma-sterilization | microwave treatment |

Visual evaluation of the samples revealed a white, an off-white or an ivory colour for samples 1d, 1e, and 2 to 6, whereas comparative sample 7 exhibited a light brown colour and sample 8 exhibited a purple-brownish colour.

In terms of the CIELAB colour space, the values given in Table 2 have been determined for the different samples using a spectrophotometer of the type UltraScan PRO from HunterLab (Murnau am Staffelsee, Germany) in reflection mode with setting RSEX, i.e. Reflectance Specular Excluded.

TABLE 2

| Sample | Initial colour | | | Colour after treatment | | |
|---|---|---|---|---|---|---|
| | L* | a* | b* | L* | a* | b* |
| 1a | 49.9 | 4.9 | 3.3 | 50.9 | 4.6 | 2.3 |
| 1b | 49.9 | 4.9 | 3.3 | 54.5 | 4.0 | 2.3 |
| 1c | 49.9 | 4.9 | 3.3 | 63.5 | 2.0 | 0.9 |
| 1d | 49.9 | 4.9 | 3.3 | 72.2 | 0.2 | 3.0 |
| 1e | 49.9 | 4.9 | 3.3 | 73.4 | −0.2 | 3.1 |
| 2 | 50.0 | 4.0 | 4.9 | 71.5 | −2.1 | 3.5 |
| 3 | 48.4 | 4.2 | 3.9 | 71.2 | −1.5 | 5.4 |
| 4 | 48.0 | 4.4 | 3.9 | 72.6 | −1.8 | 2.1 |
| 5 | 48.2 | 4.4 | 3.8 | 71.8 | −1.6 | 3.0 |
| 6 | 39.7 | 4.7 | 0.9 | 70.5 | −1.6 | 2.1 |
| 7 (comparative) | 51.7 | 4.3 | 3.7 | 61.6 | 3.4 | 10.8 |
| 8 (comparative) | 49.7 | 4.5 | 2.5 | 51.5 | 4.3 | 2.9 |

As reference, the CIELAB colour space values of a non-treated sample (i.e. without radiation sterilization according to step b) and without irradiation according to step c)) has been determined, with $L^*=71.83$, $a^*=-0.51$ and $b^*=0.75$. This value thus corresponds to (initial) colour A in terms of the present invention.

As shown by samples treated according to the present invention, an at least partial reversal of the sterilization-induced colour change can be achieved.

Specifically, samples 1d, 1e and 2 to 6 exhibit a colour C, which closely resembles the initial colour A and/or the colour of a natural tooth. In contrast, comparative samples 7 and 8 exhibit a much lower $L^*$ value of around 60 or even 50. In addition, the $b^*$ value of sample 7 is higher than 10 and thus much higher than what has been determined for colour A. For samples 7 and 8, a much higher $a^*$ value in the positive range has been determined compared to the samples according to the present invention.

The finding that for the samples irradiated by a lamp using only fiber optics a very high degree of discolouration reversal can be achieved within a relatively short time frame can be explained by the fact that the irradiating light is used at full power, i.e. at a relatively high radiant flux density.

Further experiments were carried out on a ceramic pin made of Tosoh Zirconia. Respective samples were gamma-sterilized and then irradiated using a device of the type Polylux-P for 2.5 hours (sample 9b), 18 hours (sample 9c) and 24 hours (sample 9d), whereas one gamma-sterilized sample was not irradiated for comparative reasons (sample 9a).

The present invention is further illustrated by way of the figures, of which:

Figure 1:
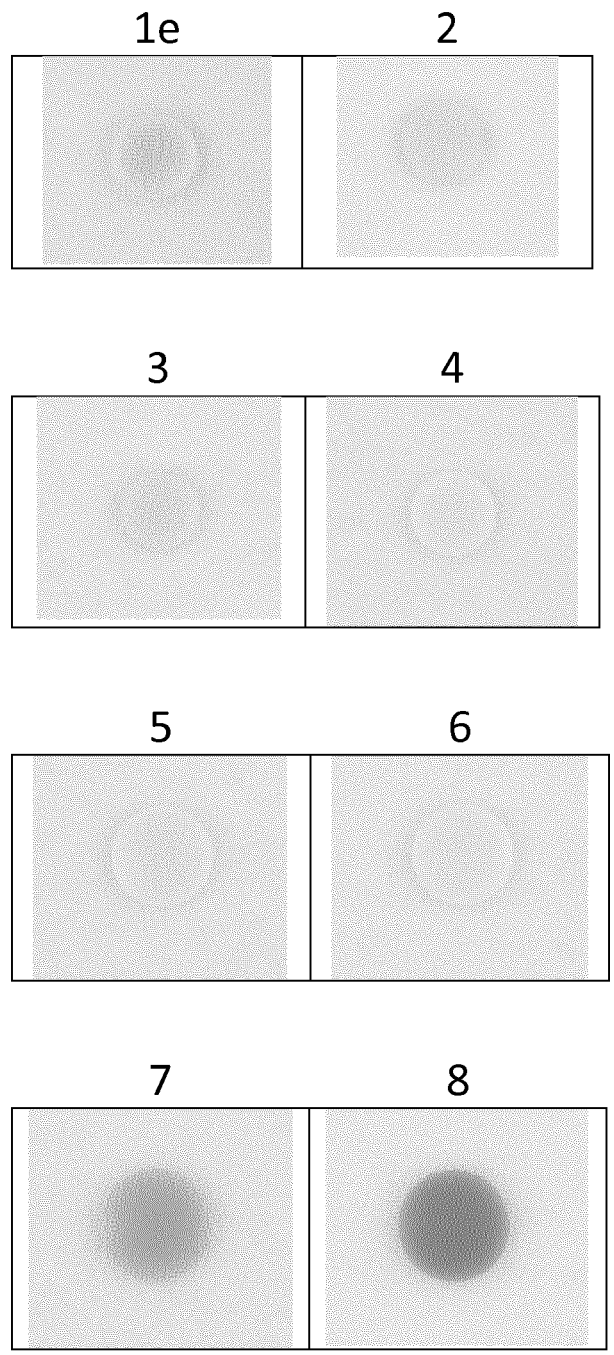
FIG. 1 shows a photograph of samples 1e and 2 to 8 discussed above.

FIG. 1 gives illustrative evidence of the reversal in discolouration obtainable by the process of the present invention. Whereas samples 1e and 2 to 6 exhibit a white, an off-white or an ivory colour closely resembling the colour of a natural tooth, comparative sample 7 exhibits a light brown colour and comparative sample 8 exhibits a purple-brownish colour.

Ultimately, the present invention allows for preparing a sterilized sample with a natural tooth colour, which makes it particular suitable for the use as a dental article.

Figure 2:
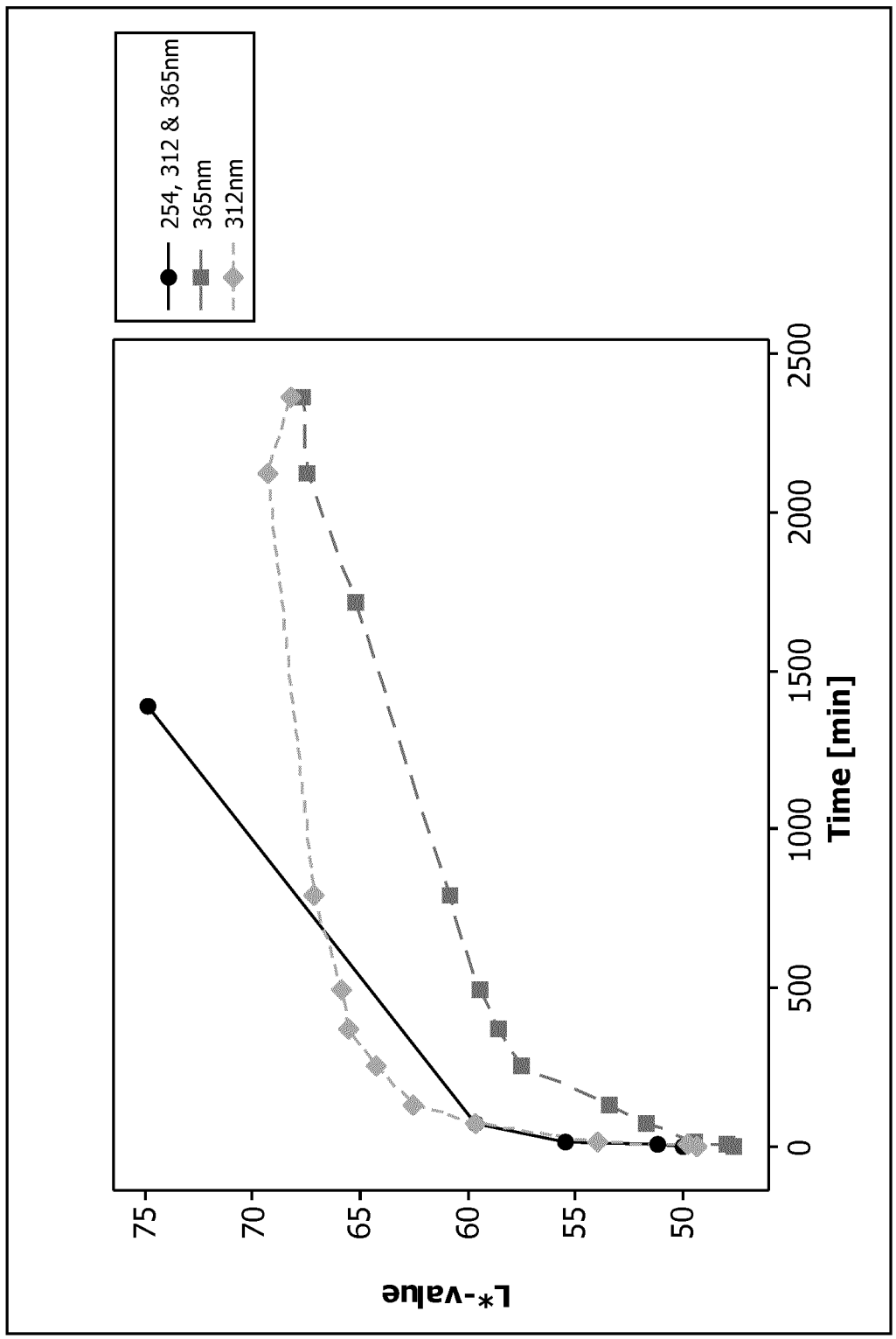
FIG. 2 shows a graphical representation of the L-value in the CIELAB colour space for different irradiation wavelengths depending on the time of irradiation.

According to FIG. 2, different irradiation wavelengths in the UV spectrum have been assessed for their effect in reversing the discolouration phenomena induced by gamma-sterilization. Specifically, the $L^*$-values of samples irradiated with electromagnetic radiation at 312 nm (diamonds), 365 nm (squares) as well as a combined irradiation at 254 nm, 312 nm and 365 nm (circles) have been assessed punctually over time. For irradiation at 254 nm and 365 nm, a lamp comprising a 4 W tube for the respective wavelength has been used (Herolab GmbH Laborgerate, Type: NU-4, Cat. No. H 466.1, Ser.-No. 13 37 003 H466.1; WEEE-Reg.-No. DE 66734561). For irradiation at 321 nm, a lamp comprising six tubes of 8 W each has been used (VILBER LOURNMAT; TFP-M/WL, Serial No. 963718).

FIG. 2 reveals that within the first hour of irradiation, the fastest increase in the $L^*$-value was achieved for the samples irradiated at 312 nm. For the samples that were subject to a combined irradiation at the three wavelengths specified above, also a relatively fast increase in the $L^*$-value was obtained, said increase being even faster than the one at 312 nm after the first hour of irradiation. After 1400 minutes of irradiation, the $L^*$-value obtained by the combined irradiation was even higher than the one obtained by irradiating at 312 nm.

Figure 3:
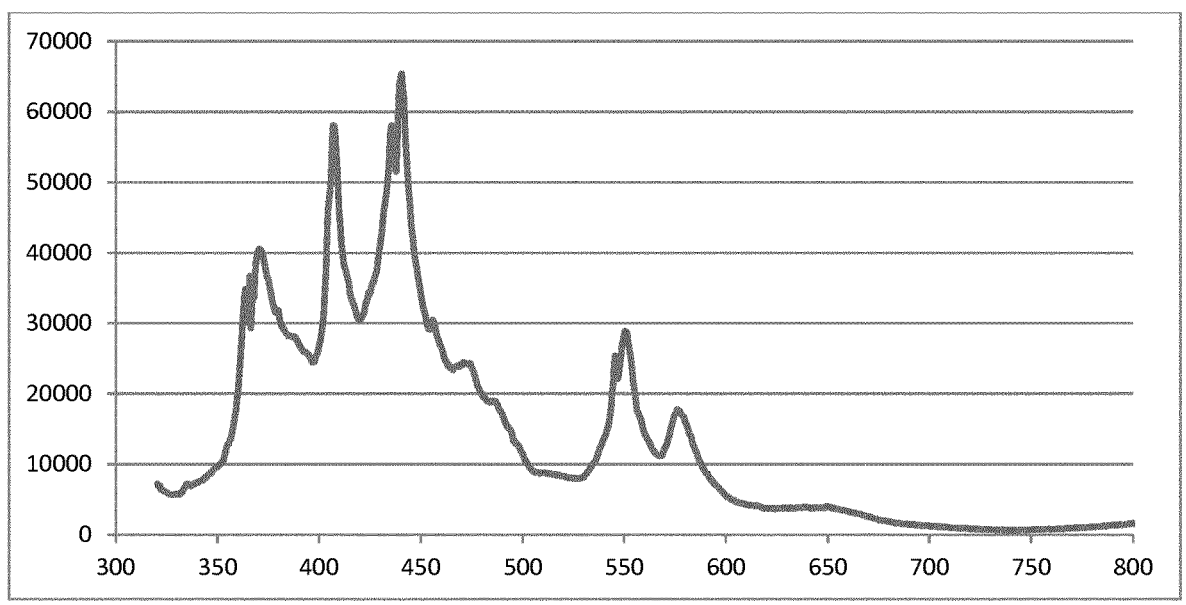
FIG. 3 shows a graphical representation of the spectrum of the lamp "Nikon Intensilight C-HGFI Precentered Fiber Illuminator" used for the light treatment according to the specific working examples (experimental set I and II) of the present invention.

FIG. 3 shows the spectrum of the specific lamp used with its relative intensities at the respective wavelength (in nm). The spectrum shows intensity peaks at about 370 nm, 410 nm, 440 nm and 550 nm, with the highest peak at 440 nm, i.e. in the blue range.

Experimental Set II

For a further experimental set-up, zirconia samples (CeramTec MZ111) grinded to a thickness of less than 0.1 mm were provided as ceramic primary body.

The samples were gamma-sterilized using a Cobalt 60 source and a dose in the range of 25-42 kGy, and then directly subjected to different treatments, namely to light treatment by exposure to the fibre optics of a "Thorlabs Inc OSL1-EC Fibre Illuminator" (in the following referred to as "Thorlabs lamp"), with a first sub-set being packed in a COC vial and a second sub-set being unpacked; or light treatment by exposure to an Intensilight lamp, with a first sub-set being packed in a COC vial and a second sub-set being unpacked.

For the treatment using the Intensilight lamp, both a mode using an adapter of the type C-HGFIB HG100 W Adapter R as well as a mode without an adapter was performed. The samples were placed orthogonally to the light source with a defined distance measured from the top of the sample to the light emitting point of the fibre optics or to the additional lens adapters.

The following treatment distances were used:

TABLE 3

| Mode | Without adapter | With adapter |
|---|---|---|
| Distance to sample | Direct: 2.0 ± 0.1 cm<br>In vial: 3.5 ± 0.1 cm | Direct: 7.0 ± 0.1 cm<br>In vial: 9.4 ± 0.1 cm |
| Illumination angle | 90° | 90° |

Figure 4:
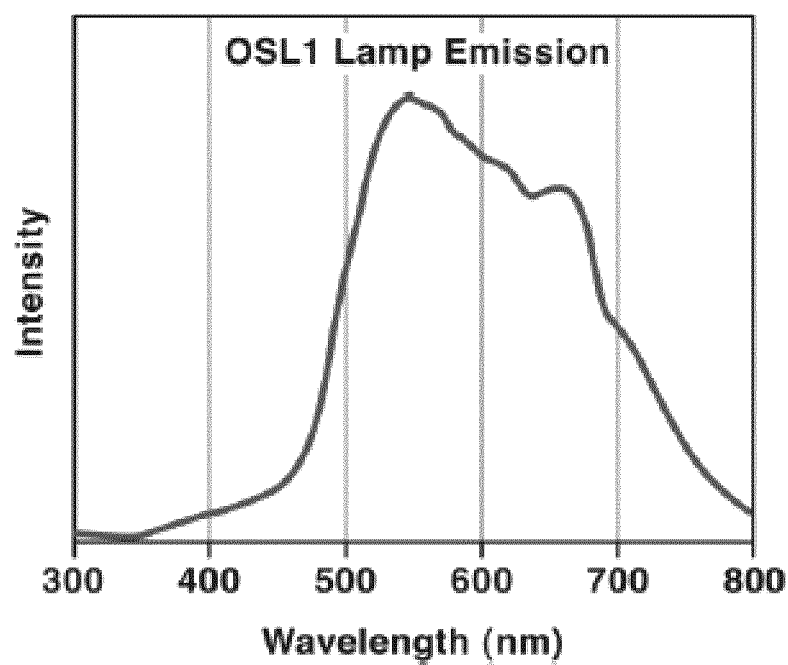
FIG. 4 shows a graphical representation of the spectrum of the lamp "Thorlabs Inc OSL1-EC Fibre Illuminator" used for the light treatment according to the specific working examples (experimental set II) of the present invention.
Figure 5:
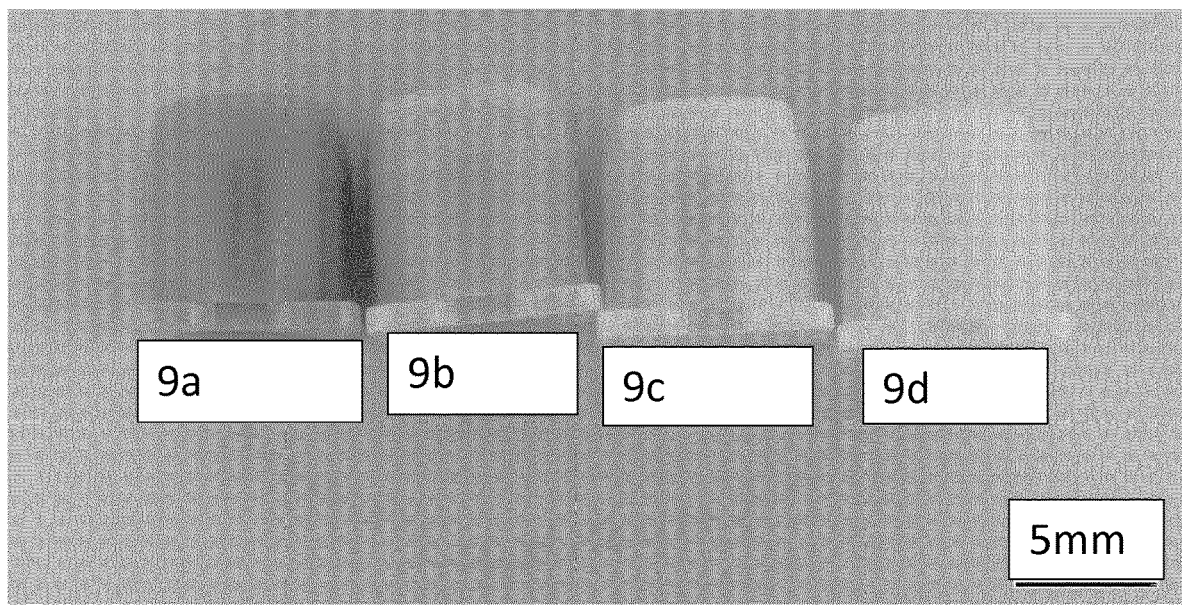
FIG. 5 shows a photograph of samples 9a to 9e discussed above.

The spectrum of the Intensilight lamp with its relative intensities at the respective wavelength (in nm) is shown in FIG. 3, as mentioned above, whereas the spectrum of the Thorlabs lamp is given in FIG. 4. While the spectrum of the Intensilight lamp shows intensity peaks at about 370 nm, 410 nm, 440 nm and 550 nm, the spectrum of the Thorlabs lamp shows intensity peaks at about 545 nm and 660 nm.

For comparative reasons, gamma-sterilized samples were subjected to the following treatment in the unpackaged state:

heat treatment at 121° C. for 30 minutes;

microwave treatment 800 W for a duration of 1 minute, followed by a duration of 4 minutes;

treatment in a demagnetizer for 190 seconds; and treatment using an $O_2$ plasma cleaner, 2 times for 2 minutes at 35 W.

The samples as well as their respective treatment are summarized in Table 4.

TABLE 4

| Sample | Treatment after sterilization |
|---|---|
| Ia | Illumination with Thorlabs lamp for 3 minutes |
| Ib | Packed in COC vial; illumination with Thorlabs lamp for 61 minutes |
| IIa | Illumination with Intensilight lamp with adapter for 317 minutes |
| IIb | Packed in COC vial; illumination with Intensilight lamp with adapter for 437 minutes |
| IIc | Packed in COC vial; illumination with Intensilight lamp with adapter + 365 nm UV light source for 437 minutes |
| IId | Packed in COC vial; illumination with Intensilight lamp with fibre optics for 55 minutes |
| IIe | Packed in COC vial filled with $H_2O$; illumination with Intensilight lamp with fibre optics for 60 minutes |
| IIf | Packed in COC vial filled with 0.9% NaCl solution; illumination with Intensilight lamp with fibre optics for 60 minutes |
| III | UV source 365 nm (4 W) for 1196 minutes |
| IV | UV source 312 nm (6*8 W) for 1196 minutes |
| V | Filter 510-560 nm (535/50) for 1680 minutes |
| VI | Filter 465-495 nm (480/30) for 900 minutes |
| VII (comparative) | demagnetizer treatment |
| VIII (comparative) | heat treatment |
| IX (comparative) | microwave treatment |
| X (comparative) | $O_2$ plasma cleaner treatment |

For the respective lamps and filters used, light measurement was performed by means of a UV enhanced silicon photodiode of the type SD100-13-23-222 (from advanced Photonix Inc.).

For calculating the flux density, the voltage was measured over the resistance (762±10.4Ω) with a precision of 0.025%. With a treatment distance of 6.5 cm and 2.5 cm, a flux density of 3'595±55 W/m² and of 20'165±284 W/m² was calculated for the Intensilight lamp, respectively. For the 510-560 nm filter, the determined flux density was 2'528 W/m² for a treatment distance of 2.5 cm and 426 W/m² for a treatment distance of 6.5 cm.

Using the 465-495 nm filter, a flux density of 255±8 W/m² was determined, the intensity being therefore only about one fifth of the intensity of the sun (with the solar constant $E_0$ being 1'367 W/m²).

After the treatments summarized in Table 4, the L*, a* and b* values of the respective samples were measured as mentioned above, the results of these measurements being summarized in Table 5.

TABLE 5

| | Colour before treatment | | | Colour after treatment | | |
|---|---|---|---|---|---|---|
| Sample | L* | a* | b* | L* | a* | b* |
| Ia | 49.47 | 4.45 | 2.64 | 66.83 | 1.93 | 12.02 |
| Ib | 50.00 | 4.95 | 3.00 | 56.87 | 2.98 | 4.99 |
| IIa | 49.98 | 3.98 | 4.88 | 72.04 | −2.15 | 3.13 |
| IIb | 48.37 | 4.15 | 3.89 | 71.58 | −1.91 | 4.01 |
| IIc | 47.70 | 4.07 | 3.01 | 70.24 | −1.56 | 4.85 |
| IId | 48.04 | 4.35 | 3.94 | 73.23 | −1.8 | 1.34 |
| IIe | 48.16 | 4.35 | 3.77 | 71.76 | −1.68 | 2.02 |
| IIf | 39.74 | 4.65 | 0.88 | 72.99 | −1.64 | 1.36 |
| III | 49.47 | 5.25 | 3.42 | 65.85 | 1.49 | 3.89 |

TABLE 5-continued

| | Colour before treatment | | | Colour after treatment | | |
|---|---|---|---|---|---|---|
| Sample | L* | a* | b* | L* | a* | b* |
| IV | 49.87 | 4.94 | 3.32 | 73.35 | −0.2 | 3.06 |
| V | 41.50 | 4.40 | 1.40 | 68.01 | −0.91 | 10.18 |
| VI | 43.16 | 4.47 | 1.26 | 71.03 | −2.30 | 8.05 |
| VII (comparative) | 44.45 | 5.54 | 4.13 | 52.92 | 3.73 | 2.07 |
| VIII (comparative) | 51.70 | 4.33 | 3.70 | 64.70 | 2.80 | 12.06 |
| IX (comparative) | 49.67 | 4.48 | 2.46 | 51.54 | 4.32 | 2.88 |
| X (comparative) | 49.60 | 4.68 | 3.14 | 52.01 | 4.33 | 3.22 |

As shown, discolouration reversal is achievable by irradiation with electromagnetic radiation emitted from the Thorlabs lamp, the Intensilight lamp and the UV sources (365 nm and 312 nm) as well as using the filters (510-560 nm and 465-495 nm). Further, discolouration reversal was achieved for both the samples packed in a COC vial as well as the unpacked samples, as can for example be seen from samples Ia and Ib as well as from IIa and IIb. This shows that light of a wavelength lying in the wavelength band according to step c) can at least partially pass the COC vial.

As shown by samples IIe and IIf, discolouration reversal is even achieved in the case where the COC vial-packed samples are stored in water or in a 0.9% NaCl solution.

Thus, the initial lightness of the gamma-sterilized zirconia can be reached by the treatment of the present invention, independent of whether the samples are packed in a COC packaging and whether the packed samples are held in a storing liquid during treatment. However, the more light is absorbed by the packaging and, as the case may be, the liquid, the longer irradiation duration is required to obtain an appearance closely matching the initial colour before sterilization.

Some samples exhibited an even higher lightness (L*) after treatment than the raw samples before gamma-sterilization. After prolonged storage for several months, samples with higher L* values than initially present (before gamma-sterilization) showed a slight decrease in the L* value, but still exhibited a lightness similar or higher than the raw samples.

Within the framework of the above experimental set-up, the best results are obtained with the Intensilight lamp. Specifically, for a zirconia sample in a COC vial (without liquid) an L* value of 70 can be reached after 14 minutes of irradiation using the Intensilight lamp.

Further testing showed that the irradiation duration to reach an L* value of 70 is 4.5 times lower when using radiation at 465 to 495 nm compared to illuminating the samples using radiation at 510 to 560 nm of the same (normalized) intensity. Nevertheless, a discolouration reversal is also achieved by using electromagnetic radiation at 510 to 560 nm and thus clearly outside the UV band. Within the framework of the experimental set-up, the best effects regarding the desired discolouration reversal are achieved by using light in a wavelength band from 312 nm to 495 nm, specifically in a wavelength band from 350 nm to 495 nm.

It was further found that for some samples the development of the L*, the a* value and the b* value do not coincide perfectly. This effect can be used to obtain a desired colour or shade by adapting the time of treatment correspondingly.

Experimental Set III

For a further experimental set, polyethylene blister-packed zirconia caps (MZ111) of a first sample I (without a bore) and of a second sample II (with a 1.8 mm diameter bore) were gamma-sterilized (using a Cobalt 60 source and a dose in the range of 25-42 kGy) and then irradiated using a device of the type Polylux-P.

After Polylux-P irradiation of samples I for 17 hours and 5 hours and of samples II for 30 hours and 45 hours, respectively, the L*, a* and b* values were measured as explained above. For comparative reasons, the L*, a* and b* values before and immediately after gamma-sterilization (i.e. before irradiation) were also measured. The results of these measurements are given in Table 6.

TABLE 6

| | treatment | L* | a* | b* |
|---|---|---|---|---|
| $I_0$ | non-gamma sterilized; non-irradiated | 73.71 | −0.52 | 3.23 |
| Ia | gamma sterilized; irradiated 17 h | 67.93 | 0.83 | 9.66 |
| Ib | gamma sterilized; irradiated 24 h | 70.06 | −0.28 | 8.06 |
| IIa | gamma sterilized; irradiated 30 h | 68.08 | −0.88 | 9.26 |
| IIb | gamma sterilized; irradiated 45 h | 70.81 | −1.52 | 6.87 |

The results show that a sufficient colour change of the packaged samples can also be achieved by using a relatively simple irradiation device, if a sufficiently long irradiation duration is chosen. Thus, the process of the present invention can be performed by using a relatively simple and small equipment and allows to obtain the desired discolouration reversal even when the ceramic body is in its packaged state.

The invention claimed is:

1. A process for the preparation of a sterilized ceramic body comprising stabilized zirconia of a defined colour, the process comprising
   a) providing a ceramic primary body comprising stabilized zirconia of a first colour A,
   b) sterilizing the ceramic primary body using radiation sterilization to form a sterilized ceramic primary body whereby the ceramic primary body undergoes a colour change to a colour B, and
   c) irradiating the sterilized ceramic primary body with electromagnetic radiation of at least one wavelength lying in a wavelength band ranging from 150 nm to 700 nm to induce an at least partial reversal of the colour change of step b) to obtain a colour C of the sterilized ceramic primary body, the colour C complying with the following requirements in the International Commission on Illumination L*a*b* (CIELAB) colour space:
   L* being from 54 to 95,
   a* being from −15 to 15 and
   b* being from −15 to 15,
   wherein step c) is carried out at a temperature below 60° C.

2. The process according to claim 1, wherein in step c) the sterilized ceramic primary body is irradiated with electromagnetic radiation of at least one wavelength lying in the wavelength band ranging from 150 nm to 600 nm.

3. The process according to claim 1, wherein the stabilized zirconia comprises vacancies in the oxygen-sublattice of its crystal structure.

4. The process according to claim 1, wherein the stabilized zirconia is yttria-stabilized zirconia.

5. The process according to claim 1, wherein the stabilized zirconia comprises extrinsic defects in the lattice of its crystal structure.

6. The process according to claim 1, wherein in step b) the ceramic primary body is sterilized using ionizing radiation sterilization.

7. The process according to claim 1, wherein in step b) an activation of colour centers in the stabilized zirconia occurs, and in step c) a transition of electrons of the colour centers from an excited state into a relaxed state is induced.

8. The process according to claim 1, wherein the wavelength band according to step c) ranges from 200 nm to 650 nm.

9. The process according to claim 1, wherein in step c) the sterilized ceramic precursor body is irradiated with electromagnetic radiation of two or more different wavelengths both lying in the wavelength band ranging from 150 to 700 nm.

10. The process according to claim 1, wherein the ceramic primary body provided in step a) is a dental article in pre-assembled and packaged form.

11. The process according to claim 1, wherein after step c) any heat treatment step is omitted.

12. The process according to claim 1, wherein the colour C complies with the requirement that L* is from 63 to 90.

13. The process according to claim 1, wherein:
   in step a), the ceramic primary body comprises yttria-stabilized zirconia of the first colour A, the ceramic primary body being in the form of a dental article containing two or more dental article components that are pre-assembled with one another and contained in an at least partially translucent packaging,
   in step b), the ceramic primary body is sterilized using gamma-sterilization whereby the ceramic primary body undergoes the colour change to the colour B, and
   in step c), the sterilized primary body is irradiated with electromagnetic radiation of at least one wavelength lying in the wavelength band ranging from 320 nm to 500 nm to induce the at least partial reversal of the colour change of step b) to the colour C, the colour C complying with the following requirements in the CIELAB colour space:
   L* being from 68 to 85,
   a* being from −10 to 10 and
   b* being from −5 to 15.

14. The process according to claim 1, wherein the colour C complies with the requirement that L* is from 70 to 75.

15. A sterilized ceramic body obtained by the process according to claim 1.

16. A dental implant system comprising a dental article composed of the sterilized ceramic body according to claim 15.

* * * * *